United States Patent [19]

Hahn et al.

[11] Patent Number: 4,751,314

[45] Date of Patent: Jun. 14, 1988

[54] PREPARATION OF TETRACHLORO-3-IMINOISOINDOLIN-1-ONE

[75] Inventors: Erwin Hahn, Heidelberg; Heinrich Kowarsch, Oberderdingen, both of Fed. Rep. of Germany

[73] Assignee: BASF Aktiengesellschaft, Ludwigshafen, Fed. Rep. of Germany

[21] Appl. No.: 907,586

[22] Filed: Sep. 15, 1986

[30] Foreign Application Priority Data

Oct. 3, 1985 [DE] Fed. Rep. of Germany ....... 3535276

[51] Int. Cl.$^4$ ........................................... C07D 209/50
[52] U.S. Cl. ................................................... 548/471
[58] Field of Search .......................................... 548/471

[56] References Cited

U.S. PATENT DOCUMENTS 3,887,581  6/1975  Kinoshita et al. .................. 548/471
4,239,686 12/1980  Misumi et al. ..................... 548/471

OTHER PUBLICATIONS

Deuvent Abstract of German Patent DE No. 2,850,782, published Nov. 1978.
J. Org. Chem. 41 (1976), 3769, J. Hall et al.

*Primary Examiner*—Mary E. Ceperley
*Attorney, Agent, or Firm*—John H. Shurtleff

[57] ABSTRACT

Tetrachloro-3-iminosisoindolin-1-one (I) or its alkali metal salt (Ia) is prepared by reacting tetrachloro-orthophthalodinitrile with lithium hydroxide, sodium hydroxide and/or potassium hydroxide in substantially anhydrous tert-butanol and, if desired, liberating (I) from (Ia) by means of a dilute acid.

17 Claims, No Drawings

PREPARATION OF TETRACHLORO-3-IMINOISOINDOLIN-1-ONE

The present invention relates to a process for the preparation of tetrachloro-3-iminoisoindolin-1-one (I) or its alkali metal salt (Ia) by reacting tetrachloro-orthophthalodinitrile with an alkali metal hydroxide in an organic solvent and, if desired, liberating (I) from (Ia) by means of a dilute acid.

German published application DAS No. 2,250,852 describes the preparation of tetrachloro-3-iminoisoindolin-1-one (I) by partial hydrolysis and cyclization of tetrachloro-ortho-phthalodinitrile (II) in the presence of alkali metals, a 1:1 mixture of water and an organic solvent advantageously being used as the solvent, and alcohols such as methanol, ethanol and isopropanol being employed as organic solvents. Tertiary alcohols are not mentioned. The resulting yields of pure compounds are about 80%, based on (II). Substantially lower yields are obtained if the water content of the solvent mixture is reduced (Comparative Example 1 with 67% and Example 7) and in particular if the reaction is carried out in anhydrous alcohols. For example, the reaction of (II) with sodium hydroxide or potassium hydroxide in anhydrous ethanol or methanol according to Examples 14 and 15 gives yields of only 43.5 and 51% of the sodium and potassium salt, respectively, of (I).

A process which gives improved yield and purity is described in German published application DAS No. 2,850,782. In this process, the halo-ortho-phthalodinitrile is reacted simultaneously with ammonia and hydrogen peroxide in a mixture of water and an organic solvent. In this reaction, large amounts of oxygen are liberated in a short time, and the process is therefore not acceptable industrially. For example, a violent explosion during the hydrolysis of o-tolunitrile with $H_2O_2$ is reported in Organ. Synthesis Vol. II, 586 (1943).

J. Org. Chem. 41 (1976), 3769 describes the conversion of simple mononitriles, including benzonitrile, to the corresponding carboxamides by hydrolysis with sodium hydroxide or potassium hydroxide in anhydrous methanol or tert-butanol. The yield of benzamide is about 90%. Mononitriles cannot be compared with the dinitriles to be used here since no cyclization takes place.

It is an object of the present invention to provide a technically simple and safe process which gives tetrachloro-3-iminoisoindolin-1-one (I) or its alkali metal salt (Ia) in high yields and good purity.

We have found that this object is achieved, and that tetrachloro-3-iminoisoindolin-1-one (I)

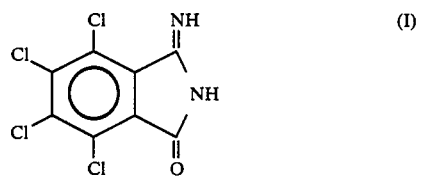

or its alkali metal salt (Ia) can particularly advantageously be prepared by reacting tetrachloro-ortho-phthalodinitrile (II)

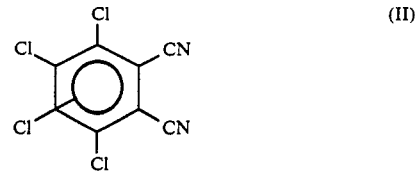

with an alkali metal hydroxide in an organic solvent and, if desired, liberating (I) from (Ia) by means of a dilute acid, if the reaction is carried out using lithium hydroxide, sodium hydroxide or potassium hydroxide in substantially anhydrous liquid tert-butanol.

The reaction according to the invention is described by the following equation:

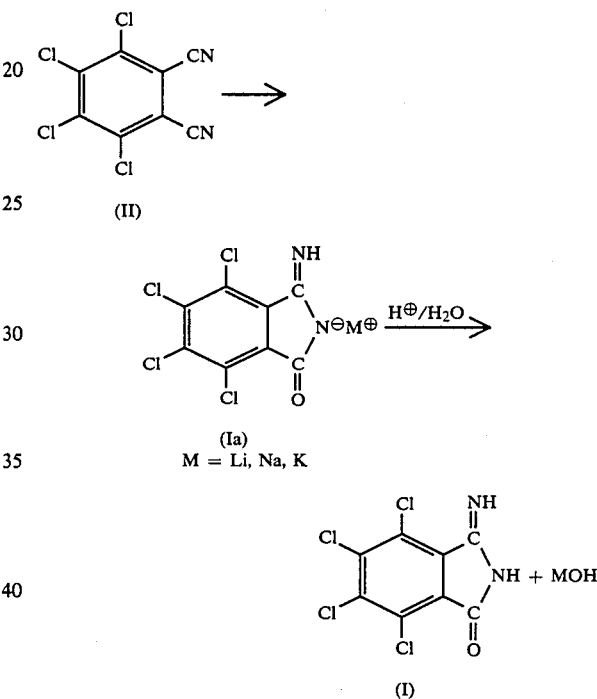

The dinitrile (II) used as a starting material can readily be prepared from ortho-phthalodinitrile in a known manner, for example by the chlorination processes described in German patent Nos. 1,643,744 and 1,932,421, these processes giving (II) in purities of from 92 to 99%.

In view of German published application DAS No. 2,250,852, it is surprising that the hydrolysis of (II) in anhydrous or substantially anhydrous tert-butanol leads to a substantial increase in yield from about 80 to more than 90% compared with the reaction in an aqueous organic medium, and that the hydrolysis in tert-butanol takes place in a substantially more advantageous manner than in other anhydrous alcohols, such as ethanol or methanol.

The water content of the tert-butanol used in the novel process is advantageously less than 5, preferably less than 1, % by weight. As the water content increases, the yields decrease.

The amount of tert-butanol is not critical. The solvent is advantageously used in an amount such that the reaction mixture remains stirrable before, during and after the reaction. The weight of tert-butanol used is preferably from 5 to 15, in particular from 6 to 10, times the weight of (II).

Suitable alkali metal hydroxides are lithium hydroxide, sodium hydroxide and potassium hydroxide and mixtures of these. The amount of alkali metal hydroxide can be varied within wide limits, but not less than 1 mole per mole of (II) should be used in order to achieve high yields. As a rule, from 1 to 5, in particular from 1.1 to 2.5, preferably from 1.2 to 2.0, moles of alkali metal hydroxide are used per mole of tetrachloro-orthophthalodinitrile (II). The hydroxide may advantageously be added in a finely powdered form to the reaction mixture.

The reaction is advantageously carried out under atmospheric pressure in liquid tert-butanol. The reaction temperatures are therefore restricted by the melting point and boiling point of the solvent. The reaction is advantageously carried out at from 26° to 80° C., in particular from 40° to 70° C., preferably from 45° to 55° C. At above 40° C., the reaction is as a rule complete after from 1 to 2 hours.

The alkali metal salt of (I), which salt is present in the reaction mixture after the reaction, can be isolated in a known manner, for example by filtration. If conversion to tetrachloro-3-iminoisoindolin-1-one is desired, either the crude reaction mixture can be acidified or, advantageously, the salt can first be isolated and then reacted with an acid. (I) is liberated from the salt by a known method, for example by reaction with a dilute mineral acid or an organic water-soluble acid, such as acetic acid.

The process is advantageously carried out as follows: the dinitrile (II) is added to the substantially anhydrous tert-butanol, and the finely divided alkali metal hydroxide is then added to the stirred mixture. After the reaction in the abovementioned temperature range, the reaction mixture is advantageously cooled to about 25° C. and filtered. The solid alkali metal salt can then be converted to the free tetrachloro-3-iminoisoindolin-1-one by, for example, introducing the salt into dilute acid.

By using substantially anhydrous tert-butanol as a solvent, the filtrate can advantageously be re-used several times, preferably from 1 to 5 times, as a reaction medium, without purification being necessary. Recycling of the tert-butanol makes the procedure particularly economical.

In the novel process, pure tetrachloro-3-iminoisoindolin-1-one (I) can be obtained in yields of from 95 to 98%, based on the starting material (II). The content of (I) is determined by titration with perchloric acid. The purity of the product, which is generally about 95%, is determined by HPLC (reversed phase high pressure liquid chromatography; Rosil 5 μm, external standard).

(I) is used as an intermediate for the preparation of pigments having good lightfastness and good heat stability.

EXAMPLE 1

400 g of liquid tert-butanol and 53 g (0.2 mole) of tetrachloro-ortho-phthalodinitrile were initially taken in a flask. 17 g (0.3 mole) of finely powdered KOH were added, after which the reaction mixture was stirred for 2 hours at 48°–52° C. and then cooled to 20° C., and the solid was filtered off over a suction filter.

The filtrate collected (about 330 g) was supplemented with fresh tert-butanol and re-used as a reaction medium.

The filtration residue was suspended in 400 ml of water, the mixture was brought to pH ≅6 by adding dilute acetic acid, and the solid was filtered off under suction, washed with water and dried under reduced pressure.

Yield: 54 g (95%) of tetrachloro-3-iminoisoindolin-1-one.

Purity according to HPLC =97.5%.

EXAMPLE 2

The process of Example 1 was repeated, except that finely divided sodium hydroxide was used instead of potassium hydroxide.

Yield: 52 g (92%) of tetrachloro-3-iminoisoindolin-1-one.

Purity according to HPLC=95%.

EXAMPLE 3

(a) The procedure described in Example 1 was followed. The tert-butanol filtrate (330 g) obtained after isolation of the reaction product was made up to 400 g by adding pure tert-butanol and used for a further reaction as described in Example 1.

Yield: 56 g (98%) of tetrachloro-3-iminoisoindolin-1-one.

Purity according to HPLC=95%.

(b) The tert-butanol filtrate obtained after isolation of the reaction product under (a) was made up to 400 g and used for a further reaction as described in Example 1.

Yield: 55 g (96.7%) of tetrachloro-3-iminoisoindolin-1-one.

Purity according to HPLC=93%.

(c) The tert-butanol filtrate obtained after isolation of the reaction product under (b) was made up to 400 g and used for a further reaction as described in Example 1.

Yield: 54 g (95%) of tetrachloro-3-iminoisoindolin-1-one.

Purity according to HPLC=92%.

COMPARATIVE EXAMPLE 1

According to German published application DAS No. 2,850,782

5 parts of sodium hydroxide are dissolved in 12.5 parts of water, and 75 parts of ethanol are added to the thoroughly stirred solution. 20 parts of 3,4,5,6-tetrachlorophthalodinitrile are added to the solution, after which stirring is continued for 5 hours at from 70° to 78° C. and the reaction mixture is then cooled to 15° C. and filtered under suction. The resulting cake is washed with water and then added to 100 parts of a 5% strength aqueous acetic acid. The mixture is stirred and filtered under suction, after which the cake obtained is washed thoroughly with water and dried under reduced pressure to give 7.16 parts of a solid, which is identified as 3-imino-4,5,6,7-tetrachloroisoindolin-1-one. The purity according to HPLC is 94.0% and the yield is 67%.

COMPARATIVE EXAMPLE 2

The procedure described in Example 1 is followed, except that a solvent mixture consisting of water and tert-butanol is used instead of tert-butanol. As shown in the table below, the yield decreases with increasing water content.

| Example | tert-butanol [g] | H₂O [g] | Yield [%] |
|---|---|---|---|
| 1 | 400 | 0 | 95 |
| 2a | 396 | 4 | 94 |
| 2b | 380 | 20 | 91 |
| 2c | 280 | 120 | 80 |
| 2d | 160 | 240 | 63 |

We claim:

1. In a process for the prepartion of an alkali metal salt (Ia) of tetrachloro-3-iminoisoindolin-1-one

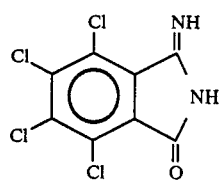  (I)

by reacting tetrachloro-ortho-phthalodinitrile

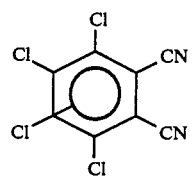  (II)

with an alkali metal hydroxide in an organic solvent, the improvement which comprises:

carrying out the reaction by bringing together the reactant (II) and lithium hydroxide, sodium hydroxide, potassium hydroxide or mixtures thereof in a substantially anhydrous liquid tert-butanol as the solvent reaction medium.

2. A process as claimed in claim 1, wherein the reaction is carried out at a temperature of about 40° to 70° C.

3. A process as claimed in claim 1, wherein the reaction is carried out at a temperature of about 45° to 55° C.

4. A process as claimed in claim 1, wherein the tert-butanol has a water content of less than 1% by weight.

5. A process as claimed in claim 1, wherein finely divided alkali metal hydroxide is used in an amount of from 1.1 to 2.5 moles per mole of tetrachloro-ortho-phthalodinitrile.

6. A process as claimed in claim 1, wherein finely divided alkali metal hydroxide is used in an amount of from 1.2 to 2.0 moles per mole of tetrachloro-ortho-phthalodinitrile.

7. A process as claimed in claim 1, wherein the alkali metal salt (Ia) is separated from the reaction medium and reacted with a dilute acid to obtain the tetrachloro-3-iminoisoindolin-1-one (I).

8. A process as claimed in claim 7, wherein the acid is selected from the group consisting of mineral acids and water-soluble organic acids.

9. A process as claimed in claim 7, wherein the acid is acetic acid.

10. A process as claimed in claim 1, wherein the reaction is carried out at a temperature of 26° to 80° C. in tert-butanol having a water content of less than 5% by weight, using a finely divided alkali metal hydroxide in an amount of from 1.0 to 5.0 moles per mole of tetrachloro-ortho-phthalodinitrile (II).

11. A process as claimed in claim 10, wherein the reaction is carried out under atmospheric pressure and at a temperature of about 40° to 70° C.

12. A process as claimed in claim 11, using tert-butanol having a water content of less than 1% by weight.

13. A process as claimed in claim 1, wherein finely divided alkali metal hydroxide is used in an amount of from 1.0 to 5.0 moles per mole of tetrachloro-ortho-phthalodinitrile.

14. A process as claimed in claim 1, wherein the weight of tert-butanol used is from 5 to 15 times the weight of tetrachloro-ortho-phthalodinitrile.

15. A process as claimed in claim 1, wherein the tert-butanol has a water content of less than 5% by weight.

16. A process as claimed in claim 1, wherein the reaction is carried out at 26°–80° C.

17. A process as claimed in claim 1 wherein the alkali metal salt (Ia) is filtered off after completing the reaction and the tert-butanol obtained as filtrate is re-used as solvent for further reactions without purification.

* * * * *

UNITED STATES PATENT AND TRADEMARK OFFICE
CERTIFICATE OF CORRECTION

PATENT NO. : 4,751,314
DATED : June 14, 1988
INVENTOR(S) : Erwin Hahn and Heinrich Kowarsch It is certified that error appears in the above-identified patent and that said Letters Patent is hereby corrected as shown below:

IN THE CLAIMS:

Claim 1, line 1: change "prepartion" to --preparation--.

Claim 1, next to last line: cancel "a".

Signed and Sealed this

Eighteenth Day of October, 1988

Attest:

DONALD J. QUIGG

Attesting Officer

Commissioner of Patents and Trademarks